United States Patent [19]

MacBrair, Jr. et al.

[11] Patent Number: 4,798,907

[45] Date of Patent: Jan. 17, 1989

[54] CONTROLLED TEMPERATURE PROCESS FOR MAKING 2,2'-OXODISUCCINATES USEFUL AS LAUNDRY DETERGENT BUILDERS

[75] Inventors: Clifford L. MacBrair, Jr.; Daniel S. Connor; Herbert C. Kretschmar, all of Cincinnati; James A. Cleary, Hamilton, all of Ohio

[73] Assignee: The Procter & Gamble Company, Cincinnati, Ohio

[21] Appl. No.: 160,615

[22] Filed: Feb. 26, 1988

[51] Int. Cl.$^4$ .................................... C07C 59/235
[52] U.S. Cl. ................................ 562/583; 562/580
[58] Field of Search ...................................... 562/583

[56] References Cited

U.S. PATENT DOCUMENTS

| | | | |
|---|---|---|---|
| Re. 28,325 | 1/1975 | White et al. | 210/58 |
| Re. 30,755 | 9/1981 | Lindsay et al. | 562/583 |
| 3,128,287 | 4/1964 | Berg et al. | 562/582 |
| 3,635,830 | 1/1972 | Lamberti et al. | 252/152 |
| 3,692,685 | 9/1972 | Lamberti et al. | 252/89 |
| 3,697,453 | 10/1972 | Tate et al. | 252/546 |
| 3,753,913 | 8/1973 | Jarowenko | 252/89 |
| 3,776,850 | 12/1973 | Pearson et al. | 252/89 |
| 3,784,486 | 1/1974 | Nelson et al. | 252/546 |
| 3,821,296 | 6/1974 | Blumberg et al. | 562/583 |
| 3,862,219 | 1/1975 | Lindsay et al. | 260/535 P |
| 3,914,297 | 10/1975 | Lamberti et al. | 260/535 P |
| 3,943,165 | 3/1976 | Lamberti | 260/484 P |
| 3,948,985 | 4/1976 | Blumbergs et al. | 250/535 P |
| 3,954,858 | 5/1976 | Lamberti et al. | 260/535 P |
| 3,965,169 | 6/1976 | Stahlheber | 260/535 P |
| 3,970,698 | 7/1976 | Lannert | 562/583 |
| 3,980,578 | 9/1976 | Nelson et al. | 252/180 |
| 3,996,150 | 12/1976 | Lamberti | 252/162 |
| 4,011,264 | 3/1977 | House | 260/535 P |
| 4,017,541 | 4/1977 | Stubbs et al. | 260/535 P |
| 4,021,376 | 5/1977 | Lamberti et al. | 252/542 |
| 4,025,450 | 5/1977 | Lamberti et al. | 252/89 R |
| 4,058,554 | 11/1977 | Gutierrez et al. | 562/583 |
| 4,066,687 | 1/1978 | Nelson et al. | 260/535 P |
| 4,079,016 | 3/1978 | Brahm et al. | 252/99 |
| 4,081,420 | 3/1978 | Lamberti | 260/31.8 R |
| 4,100,188 | 7/1978 | Kao | 260/535 P |
| 4,107,064 | 8/1978 | Nelson et al. | 252/89 R |
| 4,145,558 | 3/1979 | Gutierrez et al. | 560/180 |
| 4,152,515 | 5/1979 | Lamberti et al. | 544/107 |
| 4,228,027 | 10/1980 | Lamberti et al. | 252/174.19 |
| 4,243,820 | 1/1981 | Lamberti | 562/583 |
| 4,260,513 | 4/1981 | Lamberti et al. | 252/174.19 |
| 4,289,753 | 9/1981 | Dryoff et al. | 424/48 |
| 4,382,871 | 5/1983 | Lamberti et al. | 252/174.19 |
| 4,524,009 | 6/1985 | Yalenty | 252/89.1 |
| 4,566,984 | 1/1986 | Bush | 252/140 |
| 4,639,325 | 1/1987 | Yalenty et al. | 252/89.1 |
| 4,654,159 | 3/1987 | Bush et al. | 252/95 |
| 4,663,071 | 5/1987 | Bush et al. | 252/174.19 |
| 4,689,167 | 8/1987 | Collins et al. | 252/95 |

FOREIGN PATENT DOCUMENTS

| | | |
|---|---|---|
| 150930 | 8/1985 | European Pat. Off. . |
| 236007 | 9/1987 | European Pat. Off. . |
| 2057258 | 6/1971 | Fed. Rep. of Germany . |
| 2248708 | 4/1973 | Fed. Rep. of Germany . |
| 114420 | 8/1975 | German Democratic Rep. . |
| 49-116024 | 11/1974 | Japan . |
| 51-2708 | 1/1976 | Japan . |
| 7213538 | 4/1973 | Netherlands . |
| 707910 | 11/1970 | South Africa . |
| 1379241 | 1/1975 | United Kingdom . |
| 1392053 | 4/1975 | United Kingdom . |

OTHER PUBLICATIONS

Kemper et al., Tenside Detergents, 1975, vol. 12, pp. 47–51.
CA 101: 6267t Chemical Abstracts.
F. Loydl, Annalen, vol. 192, pp. 80–89 (1878) with translation.
Kirk-Othmer, Encyclopedia of Chemical Technology, 3rd Ed., vol. 13, pp. 103–121 (1981): Article entitled "Hydroxy Dicarboxylic Acids".
Erickson and Alberty, J. Phys. Chem., vol. 63, pp. 705–709 (1959).
CA 79: 7170 v English Abstract of FP-1.
CA 79: 80653 j English Abstract of FP-2.
CA 75: 89458 z English Abstract of FP-3.
Matzner et al., Tenside Detergents, 1973, vol. 10, pp. 239–245.
Nieuwenhuizen et al., "Synthesis and Calcium Complexation of Polycarboxylic Acids", Tenside Detergents 22 (1985) 5, pp. 247–251.
Nieuwenhuizen et al., "Polycarboxylic Acids Containing Acetal Functions: Calcium Sequestering Compounds Based on Oxidized Carbohydrates", J. Amer. Oil Chemists' Soc., vol. 60, No. 1 (Jan. 1983), pp. 120–124 at head and 44–48 at foot of page.
Rozelle and Alberty, J. Phys. Chem., vol. 61, pp. 1637–1640 (1957).
Bender and Connors, J. Amer. Chem. Soc., vol. 84, pp. 1980–1986 (1962).

*Primary Examiner*—Paul J. Killos
*Attorney, Agent, or Firm*—Richard C. Witte; Jerry J. Yetter; Thomas H. O'Flaherty

[57] ABSTRACT

High yields of 2,2'-oxodisuccinate are secured by reacting maleate and malate in aqueous alkaline media containing mixtures of particular divalent (e.g., $Ca^{2+}$) and solubilizing monovalent (e.g., $Na^+$) cations. In a preferred embodiment, the process has both an elevated temperature primary reaction step and one or more low temperature maturation steps. Yields of 2,2'-oxodisuccinate are increased and formation of fumarate byproduct is minimized.

27 Claims, No Drawings

CONTROLLED TEMPERATURE PROCESS FOR MAKING 2,2'-OXODISUCCINATES USEFUL AS LAUNDRY DETERGENT BUILDERS

FIELD OF THE INVENTION

The present invention is an improved chemical process for making 2,2'-oxodisuccinate, the tetrasodium salt of which is a known laundry detergent builder.

BACKGROUND ART

Processes for making 2,2'-oxodisuccinate in metal salt form are known and disclosed in the art. Berg, U.S. Pat. No. 3,128,287, issued Apr. 7, 1964, states that the process of his invention comprises an efficient method of producing 2,2'-oxodisuccinic acid and malic acid and provides the following disclosure:

(Col. 1, lines 32–39)

The process of this invention involves the reaction of maleic acid with a hydroxide of calcium, barium, magnesium or strontium. In general this reaction is conducted by admixing maleic acid with an excess of the hydroxide in the presence of water. The reaction mixture is then heated for from about one day to about one month at temperatures ranging from about 50° C. to reflux temperatures.

See also Col. 1, lines 65–71, which state:

As indicated above, the process of this invention produces both malic and 2,2'-oxodisuccinic acid, the ratio of these products varies with the metal hydroxide employed in the process. When strontium and barium hydroxides are employed, an almost quantitive [sic] conversion of maleic to malic acid can be effected. However, the use of calcium and magnesium hydroxide in this process produces almost an equal mixture of malic and 2,2'-oxodisuccinic acids.

See also the examples, especially Example 1.

Regardless of the efficiency of the Berg process for producing malic acid or "almost equal" mixtures thereof with 2,2'-oxodisuccinate, a synthesis directly leading to high yields of 2,2'-oxodisuccinate, with only low levels of malate or organic byproducts such as fumarate, is not disclosed. Thus, if it is desired to isolate the 2,2'-oxodisuccinate salts or formulate them into a detergent composition without automatically co-introducing substantial amounts of malate into the formulation, organic purification of the product is required. Low yield and low organic purity of the 2,2'-oxodisuccinate crude product of the Berg invention render its large-scale production commercially unattractive.

A 2,2'-oxodisuccinate synthesis process based upon Berg is also disclosed by Lamberti et al., U.S. Pat. No. 3,635,830 issued Jan. 18, 1972. The Lamberti et al. process shares the disadvantages of the Berg process.

Lamberti et al. further discloses that 2,2'-oxodisuccinate salts are useful laundry detergent builders.

Matzner et al., Tenside Detergents, 1973, Vol. 10, 239–245, writing in the context of synthesis of 2,2'-oxodisuccinates as detergent builders, state, "A more economical process would have to be developed to make this a practical (builder) candidate."

Notwithstanding the more recent disclosure of Nieuwenhuizen et al, J. Amer. Oil Chemists' Soc., Vol. 60, 1983, pages 44–48, that it is possible to conduct a laboratory synthesis of 2,2'-oxodisuccinates by addition of (preformed) malic acid to maleic acid in aqueous alkaline medium in the presence of a divalent cation, preferably $Ca^{2+}$, no commercially viable industrial process for making 2,2'-oxodisuccinates appears to have been disclosed in the art.

The Berg and Lamberti et al. patents cited above are incorporated herein by reference, especially insofar as they also include disclosure of conversion of crude calcium or magnesium-containing product of the above-cited processes to 2,2'-oxodisuccinate monovalent cation salts (e.g., sodium salts). As noted, separation of 2,2'-oxodisuccinate from other organic species such as malate is also disclosed.

In light of the foregoing, there is a clear need for an improved 2,2'-oxodisuccinate-forming process. A high-yield process, which is capable of improving the economics and/or practicality of 2,2'-oxodisuccinate production, would be especially useful to the user and manufacturer of detergent compositions. A cost-effective, large-scale process should very preferably minimize the need for organic purification of the crude 2,2'-oxodisuccinate product.

It is an object of the present invention to provide such an improved 2,2'-oxodisuccinate synthesis process, wherein the ether-bond forming reaction:

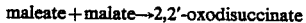

is carried out efficiently and in high yield.

It is a further object of the invention to provide a process which is usable in an overall conversion of maleic anhydride to 2,2'-oxodisuccinic acid or sodium salts thereof. Yet another object of the invention is the provision of a process for cost-effectively preparing laundry-detergent grade 2,2'-oxodisuccinate salts on a large scale, wherein organic purification is optional rather than essential.

SUMMARY OF THE INVENTION

The instant process chemically converts a particularly defined organic component to 2,2'-oxodisuccinate. Yields of 2,2'-oxodisuccinate are generally at least 80%, based on the weight of the organic component.

Whatever the precise chemical forms of the starting-materials, the process is effective when the starting-materials comprise:

I. an organic component comprising maleate and preformed malate;
II. a divalent metal cation component selected from calcium, magnesium and mixtures thereof;
III. an alkali component selected from hydroxide and hydroxide-forming (for example, oxide) anions; and the following particularly important additional component;
IV. a solubilizing monovalent cation component selected from sodium, potassium and mixtures thereof.

For best results, indeed essentially when it is desired to secure 2,2'-oxodisuccinate yields of 85% and higher, these components are used at the particular levels given in detail hereinafter. Levels and proportions at the start of the process are specified on a fully anhydride-hydrolyzed and neutralized basis and on the basis that no conversion of the organic component to 2,2'-oxodisuccinate has occurred. No components other than water and I–IV are essential in the process.

The chemist will recognize that various chemical forms of conventional starting-materials can be used. For example, a starting-material mixture made from maleic anhydride, water, D,L-malic acid, calcium hydroxide and sodium hydroxide is suitable for use herein.

Another suitable starting-material mixture can be made by conventionally reacting maleic acid and calcium carbonate in water, evolving carbon dioxide and forming calcium maleate; then admixing D,L-malic acid and sodium hydroxide.

Aqueous concentration is important in the present process. The process is generally not carried out in highly dilute aqueous media. Use of concentrated aqueous media, provided that these are not unworkably viscous, is highly preferred. The water content herein is specified on a fully hydrolyzed and neutralized basis; i.e., water removed, for example in hydrolyzing maleic anhydride to maleate, and water formed, for example in neutralizing acids and bases, are taken into account in specifying the weight percentages of water. Some evaporation losses may occur during the process; preferably, such losses are minimized by using covers or condensers on the process equipment. Alternatively, water losses can be compensated for, by adding evaporation-compensating amounts of water at any stage during the process. In any event, evaporation in the present process is not permitted to the extent of forming unworkably viscous mixtures. It is in this sense that the term "fluid" is used hereinafter in describing mixtures of the starting-materials or crude product mixtures.

As noted, the above-specified component IV is particularly important in the instant process. The specified water-soluble sodium cations, potassium cations or mixtures thereof are conventional materials. Used at levels of at least about 1% by weight of the starting-material mixture, their effect in the instant process is a significant, albeit not necessarily perfect solubilization of aqueous mixtures of components I–IV. Component IV levels in the range from about 3% to about 20% are preferred. Levels in the range from about 3% to about 16% are especially preferred. Without being bound by mechanistic theory, and irrespective of whether solubilization is fully and directly responsible for the results obtained, 2,2'-oxodisuccinate yields in excess of 80% cannot be obtained in the absence of this component.

The present process generally involves reacting the mixed starting-materials in water for a total duration of reaction of at least 12 hours, at temperatures of about 110° C. or lower (preferably in the range of 20° C. to 110° C.). Pressures are not critical. The total duration of reaction can be long, e.g., about 400 days.

It has been discovered that in order to produce 2,2'-oxodisuccinate at yields of 80% and higher, it is necessary to react fluid, aqueous alkaline mixtures of the starting-materials without overly extended exposure to high temperatures. Thus, in the instant process, the total time at any temperature above about 100° C. does not exceed about 1.5 hours and the total time at any temperature above about 90° C. does not exceed about 4.5 hours and the total time at any temperature above about 80° C. does not exceed about 13.5 hours and the total time at any temperature above about 70° C. does not exceed about 1.7 days and the total time at any temperature above about 60° C. does not exceed about 5.1 days.

It has also been found that overly extended exposure to relatively lower temperatures is also to be avoided in order to secure 2,2'-oxodisuccinate yields of 80% and higher. Thus, in the instant process, the total time at any temperature above about 50° C. does not exceed about 15 days and the total time at any temperature above about 40° C. does not exceed about 46 days and the total time at any temperature above about 30° C. does not exceed about 137 days.

When these provisions are respected, the present process reproducibly provides the desired yields of 2,2'-oxodisuccinate.

It will be appreciated that the best reaction temperatures and times will vary to some extent in dependence of the precise levels of components I–IV and in dependence of the aqueous concentration at which the process is carried out. More narrowly defined temperature-time provisions are also given hereinafter for processes according to the invention in which magnesium and potassium are used to only limited extent, as well as for processes in which only calcium and sodium cations are present by way of components II and IV respectively.

The process of the invention cannot be continued for indefinitely long periods, since 2,2'-oxodisuccinate yields reach maximum (depending on the reaction temperatures) and then tend to fall. Thus, the crude product mixtures are subjected to an organic reaction-arresting and workup procedure, which typically involves diluting the crude product mixture formed in the process and precipitating calcium carbonate using warm aqueous $Na_2CO_3/NaHCO_3$.

It is generally preferred to avoid using high temperatures, excepting for the early stages of the process. In other terms, it is preferred to avoid reheating, to high temperatures for significant periods, any crude product mixtures which have already been reacted to reach high 2,2'-oxodisuccinate yields. Thus, the preferred embodiments of the invention include isothermal processes of duration greater than 12 hours, for example at an approximately steady temperature in the range 40° C.–68° C., as well as non-isothermal processes associated with specific temperatures and times. For the highest 2,2'-oxodisuccinate yields (typically at least 85%–90%), non-isothermal processes are generally preferred. Especially preferred on the basis of yield are narrowly defined non-isothermal embodiments, having (a) an elevated temperature primary reaction procedure and (b) a lower temperature maturation procedure. In these embodiments, (a) is typically a relatively short, relatively warm reaction whilst (b) is a relatively longer reaction carried out at relatively lower temperatures (preferably, lower than step (a) by 10° C. or more).

If yields in the range about 80%–85% are acceptable, and it is desired to carry out the process relatively rapidly, the practitioner may use either isothermal or non-isothermal embodiments of the invention, such as those illustrated in detail hereinafter.

An advantage of the instant process is that only the elevated temperature primary reaction (a) need be carried out in a relatively expensive stirred reactor. The maturation procedure (b) typically requires no more than an unstirred, preferably thermally insulated, holding-tank, or even a simple tank car.

Even more significantly, the invention for the first time provides direct access to a large-scale commercial production of 2,2'-oxodisuccinate sodium salts for use as builders, for example in laundry detergents and other consumer products.

DETAILED DESCRIPTION OF THE INVENTION

Unless otherwise indicated, yields of 2,2'-oxodisuccinate and levels of other organic species herein are expressed as percentages by weight of the total of the organic species present (for example, 2,2'-oxodisuccinate plus maleate plus malate plus fumarate), as analyzed by high-performance liquid chromatography (HPLC).

The above-summarized patent and journal literature provides aqueous processes for manufacturing 2,2'-oxodisuccinate from starting-materials comprising the components I organic starting-material component comprising maleate, II divalent metal cation component and III alkali component. The processes partially convert the organic starting-material component to 2,2'-oxodisuccinate. Though not specifically mentioned in any detail, these processes inherently tend to form a fumarate byproduct.

The instant invention is of an improvement whereby a 2,2'-oxodisuccinate yield of about 80% or higher is secured. The improvement comprises: A. selecting starting-materials which comprise: I an organic component comprising maleate and preformed malate at a maleate:malate mole ratio in the range from about 0.7:1 to about 2.0:1, II a divalent metal cation component selected from calcium, magnesium and mixtures thereof at a divalent cation component:organic component mole ratio in the range from about 0.1:1 to about 0.95:1; III an alkali component selected from hydroxide and hydroxide-forming anions; and, additionally, IV a solubilizing monovalent cation component selected from sodium, potassium and mixtures thereof. Also, B. the process is conducted in a fluid, aqueous alkaline mixture of said starting-materials having the following net concentrations by weight: water: no more than about 75%; alkali component III, expressed as net excess hydroxide: at least about 0.0001%; and solubilizing monovalent cation component IV: at least about 1%.

According to the invention, the mixture B is reacted for a period sufficient to attain said 2,2'-oxodisuccinate yield at temperatures in the range from about 20° C. to about 110° C., and the reaction is then immediately arrested. In general, the following provisions are respected: the total duration of reaction is not less than about 12 hours and not more than about 400 days; the total time at any temperature above about 100° C. does not exceed about 1.5 hours; the total time at any temperature above about 90° C. does not exceed about 4.5 hours; the total time at any temperature above about 80° C. does not exceed about 13.5 hours; the total time at any temperature above about 70° C. does not exceed about 1.7 days; the total time at any temperature above about 60° C. does not exceed about 5.1 days; the total time at any temperature above about 50° C. does not exceed about 15 days; the total time at any temperature above about 40° C. does not exceed about 46 days and the total time at any temperature above about 30° C. does not exceed about 137 days.

It has been found desirable to have only relatively low levels of magnesium or potassium present. Thus, preferred embodiments of the invention include those comprising A. selecting starting-materials which comprise: I an organic component comprising maleate and preformed malate at a maleate:malate mole ratio in the range from about 0.9:1 to about 1.8:1; II a divalent metal cation component selected from calcium and mixtures thereof with magnesium, the calcium:magnesium mole ratio ranging from about 1.0:0.0 to about 0.9:0.1; at a divalent cation component:organic component mole ratio in the range from about 0.2:1 to about 0.85:1; III an alkali component selected from hydroxide and hydroxide-forming anions; and, additionally, IV a solubilizing monovalent cation component selected from sodium and mixtures thereof with potassium, the sodium:potassium mole ratio ranging from about 1.0:0.0 (i.e., no potassium present) to about 0.9:0.1 (i.e., a low level of potassium present); and B. conducting the process in a fluid, aqueous alkaline mixture of said starting-materials having the following net concentrations by weight: water: from about 25% to about 60%; alkali component III, expressed as net excess hydroxide: from about 0.0001% to about 2%; and solubilizing monovalent cation component IV: from about 3% to about 20%. This preferred embodiment further involves reacting said mixture at temperatures in the range about 20° C. to about 110° C. for a period sufficient to attain the 80%, or higher, 2,2'-oxodisuccinate yield, and arresting the reaction; provided that the total duration of reaction is not less than about 12 hours and not more than about 240 days and further provided that: the total time at any temperature above about 100° C. does not exceed about 1 hour and the total time at any temperature above about 90° C. does not exceed about 3 hours and the total time at any temperature above about 80° C. does not exceed about 8 hours and the total time at any temperature above about 70° C. does not exceed about 1 day and the total time at any temperature above about 60° C. does not exceed about 3 days and the total time at any temperature above about 50° C. does not exceed about 9 days and the total time at any temperature above about 40° C. does not exceed about 27 days and the total time at any temperature above about 30° C. does not exceed about 81 days.

When using only sodium and calcium as essential monovalent and divalent metal cations, the invention has preferred embodiments which comprise A. selecting starting-materials which comprise I an organic component comprising maleate and preformed malate at a maleate:malate mole ratio in the range from about 1.05:1 to about 1.7:1, more preferably, from about 1.1:1 to about 1.6:1; II a divalent metal cation component selected from calcium at a divalent cation component:organic component mole ratio in the range from about 0.25:1 to about 0.80:1, more preferably, from about 0.35:1 to about 0.80:1, III an alkali component selected from hydroxide and hydroxide-forming anions; and, additionally, IV a single solubilizing monovalent cation component, namely sodium; and conducting the process in a fluid, aqueous alkaline mixture of said starting-materials having the following net concentrations by weight: water: from about 30% to about 50% (more preferably, from about 30% to about 45%); alkali component III, expressed as net excess hydroxide: from about 0.01% to about 1.5% (more preferably, from about 0.05% to about 1%); and solubilizing monovalent cation component IV: from about 3% to about 16% (more preferably, from about 3.5% to about 12%). In these embodiments, the fluid, aqueous alkaline mixture of starting-materials is reacted at temperatures in the range about 20° C. to about 110° C. for a period sufficient to attain said 2,2'-oxodisuccinate yield, and the reaction is then arrested; provided that the total duration of reaction is not less than about 12 hours and not more than about 40 days and further provided that: the total time at any temperature above above about 100° C. does not exceed about 30 minutes and the total time at any temperature above about 90° C. does not exceed about 1.5 hours and the total time at any temperature above about 80° C. does not exceed about 5 hours and the total time at any temperature above about 70° C. does not exceed about 15 hours and the total time at any temperature above about 65° C. does not exceed about 1 day and the total time at any temperature above about 60° C. does not exceed about 1.5 days and the total time at any temperature above about 50° C. does not exceed about 8 days.

As noted in summary, the invention has both isothermal and non-isothermal preferred embodiments. Non-isothermal preferred embodiments include those which consistently afford the higher (e.g., greater than 85%) 2,2'-oxodisuccinate yields.

Embodiments of the invention wherein the components I–IV and water are reacted together non-isothermally include those using the following sequence of steps: (a) an elevated temperature primary reaction procedure of duration about 10 minutes to about 8 hours, at about 50° C. to about 110° C., contacting the starting-materials to form said fluid, aqueous alkaline mixture and reacting to form a crude product mixture, also fluid, comprising freshly formed 2,2'-oxodisuccinate together with unreacted maleate and malate and immediately; (b) in a lower temperature maturation procedure of duration about 1 day to about 30 days, reducing the temperature of the crude product mixture of step (a) in one or more steps (preferably to temperatures in the range from about 20° C. to about 45° C.) whilst retaining fluidity and continuing to react said crude product mixture, for a period sufficient to chemically combine and form 2,2'-oxodisuccinate from said maleate and malate; thereby increasing the overall proportion of 2,2'-oxodisuccinate present in said crude product mixture while achieving control of the rate of formation of fumarate byproduct; and (c) arresting said lower temperature maturation procedure.

In other non-isothermal embodiments, the procedure (b) can be carried out at temperatures above the 20° C.–45° C. temperature range, but the 2,2'-oxodisuccinate yield maxima will then tend to fall.

More generally, non-isothermal embodiments of the invention need not comprise a sequence of sharply differing temperature steps; for example, continuous cooling from elevated to lower temperatures is perfectly acceptable. Such continuous cooling processes evidently have no extended period of maintaining the reaction at any one temperature, even at the specified high and low temperature limits.

In the non-isothermal preferred embodiments, highly preferred starting-compositions involve A. selecting starting-materials which comprise: I an organic component comprising maleate and preformed malate at a maleate:malate mole ratio in the range from about 1.15:1 to about 1.40:1; II a divalent metal cation component selected from calcium, at a divalent cation component:organic component mole ratio in the range from about 0.41:1 to about 0.76:1; III an alkali component selected from hydroxide and hydroxide-forming anions; and, additionally, IV a solubilizing monovalent cation component, which is sodiium; and B. conducting the process in a fluid, aqueous alkaline mixture of said starting-materials having the following net concentrations by weight: water: from about 35.0% to about 41.08%; alkali component III, expressed as net excess hydroxide: from about 0.10% to about 0.91%; and solubilizing monovalent cation component IV: from about 3.9% to about 10.6%.

Even more preferably for maximizing the 2,2'-oxodisuccinate yield, the invention has embodiments wherein step (a) is carried out at elevated temperatures in the range of from about 50° C. to about 110° C. and has a duration of from about 10 minutes to about 5 hours, provided that in step (a), said elevated temperatures are not in excess of about 100° C. for times greater than about 15 minutes and are not in excess of about 80° C. for times greater than about 30 minutes; and wherein step (b) comprises reducing the temperature to lower temperatures in the range of from about 20° C. to about 40° C. in a time less than about 2 hours and maintaining said lower temperatures; step (b) having a duration of from about 1 day to 21 days in total; provided that in step (b), said lower temperatures are not in excess of about 36° C. for times greater than about 7 days and are not in excess of about 30° C. for times greater than about 14 days.

As noted, the chemist has numerous alternative choices of starting-materials. It is preferred to have at least one maleate compound selected from the group consisting of maleic anhydride and maleic acid, together with at least one malate compound selected from the group consisting of malic acid and stereoisomers thereof.

There are several possible sources of sodium for use in the process. It is preferred to use starting-materials which include at least one sodium-containing compound selected from the group consisting of disodium maleate, disodium malate, sodium carbonate, sodium bicarbonate and sodium hydroxide.

Common calcium-containing starting-materials include one or more compounds selected from the group consisting of calcium maleate, calcium malate, calcium hydroxide, calcium oxide and calcium carbonate. Certain more unusual chemical forms of calcium-containing starting-material may also be used. For example, a specific form of calcium malate-hydroxide, such as is illustrated in Example 9 hereinafter, is suitable for use in the process.

The starting-materials also generally include at least one compound forming hydroxide anions in water. Such compounds preferably include one or more compounds selected from the group consisting of sodium hydroxide, calcium hydroxide and calcium oxide.

Less desirably, the starting-materials can include various conventional potassium or magnesium salts, such as potassium hydroxide, magnesium hydroxide, or the like.

Whatever the chemical forms of the starting-materials, what is essential herein is to combine them to provide the above-specified ratios and proportions of the components I–IV and water.

One simple full set of starting-materials consists essentially of maleic anhydride, D,L-malic acid, sodiium hydroxide and calcium hydroxide. In a preferred process using these starting-materials, the step (a) elevated temperature reaction procedure comprises adding maleic anhydride over a period of about 10 to about 30 minutes, as portions of solid or as liquid at temperatures above the melting-point but preferably not exceeding about 100° C., to a continuously stirred preformed mixture of said D,L-malic acid, calcium hydroxide and sodium hydroxide, the preformed mixture having an initial temperature in the range from about 50° C. to about 85° C., rising exothermically to a maximum of from about 100° C. to about 110° C. during the course of maleic anhydride addition, thereby forming a crude product mixture.

In this embodiment, upon ending the above-outlined procedure (a), the crude product mixture is substantially homogeneous and has an organic composition, as a percentage by weight based on 2,2'-oxodisuccinate plus maleate plus malate plus fumarate, of: 2,2'- oxodisuccinate: from about 20% to about 45%; fumarate: from about 1% to about 2% and maleate plus malate: from about 53% to about 79%.

Step (b), i.e., the lower temperature maturation procedure immediately follows step (a) and comprises cooling said crude product mixture to a lower temperature of from about 36° C. to about 40° C. within a time of about 10 minutes to about 2 hours, and storing said crude product mixture at said lower temperature; step (b) having a duration of from about 2 days to about 7 days in total.

At the end of the above-outlined maturation procedure, the crude product of this embodiment of the process typically has an organic composition comprising, as a percentage by weight based on 2,2'-oxodisuccinate plus maleate plus malate plus fumarate, of: 2,2'-oxodisuccinate: at least about 82%; fumarate: from about 1.5% to about 5.7% and maleate plus malate: from about 7.3% to about 16.5%.

More than one lower temperature maturation step can be encompassed within the procedure (b); thus the invention has embodiments wherein step (b) comprises: cooling said crude product mixture to a first lower temperature in the range from about 36° C. to about 40° C. within a time of about 10 minutes to about 1 hour, and storing said crude product mixture at said first lower temperature; step (i) having a duration of from about 2 days to about 7 days; followed immediately by cooling said crude product mixture to a second lower temperature in the range from about 25° C. to about 30° C. within a time of about 10 minutes to about 6 hours, and storing said crude product mixture at said second lower temperature; step (ii) having a duration of from about 7 days to about 14 days.

At the end of such a two-step or multi-step procedure (b), the crude product of this embodiment has the following organic composition, as a percentage by weight based on 2,2'-oxodisuccinate plus maleate plus malate plus fumarate, 2,2'-oxodisuccinate: at least about 90% (typically, 90%–95%); fumarate: from about 2% to about 6% and maleate, malate or mixtures thereof: to 100%.

In general, it is essential to arrest all organic product and byproduct-forming chemical reaction at the end of the lower temperature maturation procedure, to avoid the 2,2'-oxodisuccinate content of the crude product falling after it reaches the maximum made possible by the process. When the 2,2'-oxodisuccinate content falls, the levels of fumarate byproduct concurrently begin to increase. Thus, in a preferred embodiment of the invention, immediately after the lower temperature maturation procedure, reaction (b) is arrested by (c) treating said crude product mixture with a warm aqueous mixture of sodium carbonate and sodium bicarbonate, thereby precipitating calcium carbonate.

Provided that the practitioner respects the overall temperature-time limitations given supra, and thereby avoids over-extended periods of reacting the starting-materials at particular temperatures, he may flexibly opt to carry out one or more lower temperature maturation steps in a procedure of type (b), based upon monitoring the organic composition of the reaction mixture or crude product mixture.

When carrying out such monitoring, for example by high-performance liquid chromatography (HPLC), monitoring of 2,2'-oxodisuccinate level or of fumarate level is quite sufficient.

Naturally, the practitioner will recognize that fumarate is an impurity common in maleate and malate feedstocks (as well as being a byproduct, as noted, in the instant process). Therefore, when monitoring fumarate levels in the instant process, the practitioner will begin the process using starting-materials of known fumarate content.

The invention thus has preferred embodiments which include a process wherein the starting-materials have a known fumarate level, e.g., when they comprise no more than about 0.01 moles of fumarate impurity per mole of said maleate plus said preformed malate, and wherein step (a) is carried out at elevated temperatures in the range from about 50° C. to about 110° C., provided that in step (a), said elevated temperatures are not in excess of about 100° C. for times greater than about 15 minutes and are not in excess of about 80° C. for times greater than about 1 hour; and wherein step (b) comprises reducing the temperature to lower temperatures in the range of from about 20° C. to about 40° C., provided that in step (b), said lower temperatures are not in excess of about 36° C. for times greater than about 7 days and are not in excess of about 30° C. for times greater than about 14 days; step (a) being ended and step (b) being undertaken at any time corresponding with a net increase in fumarate level, based upon HPLC-analysis of the crude product mixture, in the range from about 0.5% to 5%.

Even more rigorously limiting increases in fumarate level by analytical monitoring of the process further increases yield. To illustrate, the above embodiment can be modified by ending step (a) and undertaking step (b) at any time corresponding with a net increase in fumarate level, base upon HPLC-analysis of the crude product mixture, in the range from about 0.5% to about 2.5%; and wherein step (b) is ended and step (c) is undertaken immediately upon reaching an HPLC-based 2,2'-oxodisuccinate yield of at least about 85%.

The practitioner of the invention may not wish to realize the maximum 2,2'-oxodisuccinate yields, preferring to save time and secure good 2,2'-oxodisuccinate yields in a typical range 80%–85%. In this event he may opt to carry out step (a) at elevated temperatures in the range from about 70° C. to about 110° C., in a period of from about 4 hours to about 5 hours, provided that in step (a), said elevated temperatures are not in excess of about 100° C. for times greater than about 15 minutes and are not in excess of about 80° C. for times greater than about 30 minutes. In step (b), the temperature is reduced to lower temperatures in the range of from about 50° C. to about 59° C. in a period of from about 15 minutes to about 1 hour, and the lower temperatures are maintained, step (b) having a duration of from about 7 hours to about 20 hours in total.

In contrast, another preferred embodiment of the invention having better yields but taking more time, is as follows: step (a) is carried out at elevated temperatures in the range from about 75° C. to about 110° C., in a period of from about 20 minutes to about 1 hour, provided that in step (a), said elevated temperatures are not in excess of about 100° C. for times greater than about 15 minutes and are not in excess of about 80° C. for times greater than about 30 minutes; and step (b) comprises reducing the temperature to lower temperatures in the range of from about 35° C. to about 45° C. in a period of from about 15 minutes to about 1 hour, and maintaining said lower temperatures; step (b) having a duration of from about 48 hours to about 240 hours in total; whereby a 2,2'-oxodisuccinate yield of at least about 85% is secured.

A preferred procedure to be followed when using calcium carbonate as a calcium source, i.e., as a calcium starting-material, in the instant process is as follows; preformed malic acid, sodium hydroxide, a maleate reactant selected from maleic anhydride, maleic acid and mixtures thereof, and a calcium reactant selected from calcium carbonate and mixtures thereof with calcium hydroxide are reacted according to the immediately consecutive steps: (i) mixing calcium carbonate, water, malic acid and a proportion of said maleate reactant, allowing complete evolution of carbon dioxide and forming an acidic mixture; (ii) adding sodium hydroxide or a mixture thereof with calcium hydroxide, to the acidic mixture of step (i), forming a sodium cation-containing alkaline mixture; (iii) in a period of duration about 1 hour or less, adding the remainder of said maleate reactant to the stirred sodium cation-containing alkaline mixture of step (ii), at temperatures in the range from about 75° C. to about 110° C., having at the end of the step (iii) addition a net hydroxide excess $M_{OH}$; (iv) in a period of duration about 1 hour or less, cooling the mixture formed in step (iii) to a temperature in the range from about 35° C. to about 45° C.; (v) at said temperature in the range from about 35° C. to about 45° C., continuing to react the mixture of step (iv); the duration of step (v) being from about 48 hours to about 240 hours, whereby a crude product having a HPLC yield of at least 80% 2,2'-oxodisuccinate is secured; and (vi) diluting the product of step (v) with water and precipitating calcium carbonate therefrom; thereby arresting the step (iv) reaction and depleting the level of calcium; provided that in step (iii) and (iv) together; the total time at any temperature above about 100° C. does not exceed about 15 minutes; the total time at any temperature above about 90° C. does not exceed about 30 minutes; the total time at any temperature above about 80° C. does not exceed about 2 hours; the total time at any temperature above about 70° C. does not exceed about 6 hours; and the total time at any temperature above about 65° C. does not exceed about 12 hours; and provided that for each mole of preformed malic acid reacted, the total molar amount of maleate reactant is about 1.1 to about 1.6 moles; the total molar amount of calcium reactant, is from about 0.9 to about 1.65 moles; the total molar amount of sodium hydroxide, is from about 0.92 to about 3.7 moles; the net hydroxide excess in step (iii), $M_{OH}$, is from about 0.02 to about 0.3 moles; and further provided that for each mole of preformed malic acid reacted (i.e., charged in the reactor), the total net amount of water added in steps (i), (ii) and (iii) together, allowing for evaporation losses, is no less than about 189 grams and no more than about 282 grams.

The above procedure has advantages in that calcium carbonate can be recycled by (vii) filtering the mixture of step (vi) to secure a filter-cake and (viii) using the filter-cake of step (vii) as recycled source of calcium carbonate in step (i).

Returning to the isothermal reaction procedures that can also be practiced in accordance with the invention, the term "isothermal" is deserving of comment. Isothermal processes herein are those in which substantially constant temperature is maintained, from the time at which at least some of each of the essential components I-IV is present in a fluid, aqueous, alkaline mixture (i.e., from the time at which it is possible for 2,2'-oxodisuccinate formation to occur), until the time at which reaction is arrested as defined herinabove. The term "substantially constant" in this context makes allowance for practical considerations, such as precision of conventional process control equipment, e.g., thermostats.

Isothermal processess herein include those in which the divalent cation component:organic component mole ratio is in the range from about 0.40:1 to about 0.75:1, and in which the process is conducted at a concentration of water in the range from about 35% to about 41% and comprises reacting said mixture at a temperature in the range from about 50° C. to about 68° C. for a period of from about 48 hours to about 240 hours, then arresting the reaction.

Other isothermal processes herein, such as those carried out at about 40° C. to about 49° C., are also effective, but are of longer duration.

Crude product mixtures in the present process are unique. After carrying out the instant process using the details of temperature and time or HPLC monitoring given herein, the practitioner may turn to very simple characteristics of the crude product mixture, such as visually, optically or, especially, rheologically measurable characteristics of the crude product mixture, as they change during the process, for aid in monitoring the process.

Crude product mixtures made by reacting the starting-materials according to the invention have the following characteristics as soon as they are sufficiently reacted to commence a lower-temperature maturation procedure such as (b) described above: taking the starting-materials, maleic anhydride and an aqueous alkaline mixture of D,L-malic acid, sodium hydroxide and calcium hydroxide as a simple illustration, the mixture formed upon adding some maleic anhydride to the aqueous alkaline malate-containing mixture in step (a) is a two-phase mixture consisting of a liquid phase, in major proportion, and a solid phase, in minor proportion. The proportion of the solid phase decreases and the viscosity of the liquid phase increases during addition of the remaining maleic anhydride and thereafter, so that, at the end of step (a), a crude product mixture is formed which is pumpable, i.e., fluid, and which appears substantially homogeneous to the eye.

Adding viscosity data, the Brookfield relative viscosity of the crude product mixtures in the process typically increases during the lower temperature maturation procedure (b) from an initial value of less than about 100 centipoise to a final value at the end of procedure (b) which is in the range about 1000 centipoise to about 100,000 centipoise, as measured under Brookfield test conditions of 22° C./20 r.p.m. Preferably, while the crude product mixture generally remains pumpable, the viscosity increase during the process is of 3000 centipoise or more. Also, the crude product mixtures typically fail to separate into visual distinct layers upon standing unstirred, e.g., at test temperatures of about 60° C. for a test period of about 48 hours.

Expressing the hereinbefore described ratios and proportions of reactants in certain preferred embodiments of the instant process on a weight basis is helpful in allowing the practitioner of the invention to carry out the process with excellent results. Thus, the invention encompasses conducting the process in a fluid, aqueous alkaline mixture of said starting-materials, the amounts of which are calculated to deliver by weight, expressed on a fully hydrolyzed and neutralized basis assuming no 2,2'-oxodisuccinate or fumarate formation and no maleate→malate interconversion: water: from about 30.0% to about 45.0%; net excess hydroxide: from about 0.05% to about 1.0%; sodium: from about 3.4% to about 13%; calcium: from about 4.5% to about 13%; maleate: from about 19.1% to about 28.48% and preformed malate: from about 16.5% to about 26.8%.

When the process is carried out with inclusion of recycled fumarate and/or 2,2'-oxodisuccinate (for example, entrained in a recycled calcium carbonate filter-cake) or with inclusion of fumarate and/or 2,2'-oxodisuccinate starting-material impurities (for example, as can be present as fumaric acid in D,L-malic acid, or as can be present as calcium fumarate in calcium malate), then the above weight percentages should be adjusted to allow for their presence. Typically, recycled 2,2'-oxodisuccinate levels at the start of the process do not exceed about 2%. Likewise, fumarate recycle or fumarate impurity levels at the start of the process typically do not exceed about 2%. Naturally, it is preferred to use fumarate-free starting-materials.

Conventional maleate, malate and fumarate chemistry is well reviewed in "Maleic Anhydride", B. C. Trivedi and B. M. Culbertson, Plenum Press, N.Y., 1982 and in Kirk-Othmer, Encyclopedia of Chemical Technology, 3rd Ed., 1981, Vol. 13, pp. 103-121 and Vol. 14, pp. 770-793, all incorporated herein by reference.

Unless otherwise indicated, all ratios herein are mole ratios and all percentages are by weight.

The invention is further illustrated by the following non-limiting examples:

EXAMPLE I

Equipment:

The following equipment is made ready: open-topped reactor drum of 316 stainless steel (SS), 60 liter capacity, equipped with removable plastic cover and with twin rotor turbine stirrer driven by a shaft connected above to a compressed air motor; doublewall, insulated vessel of SS or equivalent Dewar vessel having 200 liter capacity, suitable for substantially complete immersion of the reactor drum, with a good space, at least 8 inches, around the reactor drum as well as between the bottom of the reactor drum and the bottom inner wall of the Dewar vessel. The Dewar vessel has steam and hot and cold water inlets and outlets. Also provided are steam sprayer coils; 3 kW electrically powered and thermostatically controlled immersion heater; immersible water circulation pump; and removable cover for minimizing evaporation of heating water, capable of covering the annular space between the reactor drum and the inner wall of the Dewar vessel; thermometers both for reactor drum and Dewar vessel.

Assembly:

The steam sprayer coils are placed around the reactor drum and the drum and surrounding coils are placed in the Dewar vessel. The remaining equipment is assembled so as to allow rapid but controlled heating of the reactor drum. Such heating involves any of: passage of hot water through the Dewar vessel, electrical heating and recirculation of water in the Dewar vessel, or direct steam heating of the reactor drum by steam sprayed through the sprayer coils onto the outer walls and bottom of the reactor drum. The equipment is also assembled so as to allow rapid but controlled cooling, by passage of tempered or cold water into the Dewar vessel with drainage of hot water, or by addition of ice to the water in the Dewar vessel.

Precontacting of alkali, malate, sodium and calcium:

A 50% aqueous solution of sodium hydroxide (total weight 17520 g, contains 219 moles NaOH, Fisher) is added with stirring to distilled water (14360 g). The caustic solution is then heated to 50° C. Over a period of 9 minutes, granular D,L-malic acid (13400 g, 100 moles, Aldrich, 99%) is added in portions to the vortex of the stirred caustic solution, cooling as necessary to maintain a temperature in the range about 80° C.-95° C. Over a period of 6 minutes, powdered calcium hydroxide (9176 g, 124 moles, Aldrich, 90%+, ACS grade) is now added in portions to the vortex of the alkaline Na/Ca malate mixture, maintaining the temperature. Over a period of 20 minutes, stirring is continued without substantially altering the temperature. At the end of this period, the temperature of the alkaline Na/Ca malate mixture is 85° C.

(a) Contacting and primary reaction:

Over a 14 minute period, maleic anhydride (12544 g, 128 moles, Aldrich, 99%, briquettes, freshly crushed) is added to the vortex of the stirred alkaline Na/Ca malate mixture at a steady rate. During this period, an exotherm carries the temperature of the reaction from 85° C. to a maximum in the range 100° C.-110° C., more typically 103° C.-105° C. Also during this period, within about 10 minutes of starting to add maleic anhydride, the visual appearance of the reaction mixture changes from that of a chalky suspension typical of calcium salts to that of a homogenous but somewhat opaque and honeylike crude product mixture.

At the end of the maleic anhydride addition period, cooling is applied over a period of 16 minutes bringing the reaction temperature to about 76° C.-78° C. One operator now characterizes the crude product mixture, whilst a second operator continues the process.

The first operator finds that the viscosity has increased relative to the starting-point of maleic anhydride addition. A first high performance liquid chromatography (HLPC) sample, is taken by the first operator at the 30 minute point. See the analytical protocol hereinafter for details of the HPLC analysis. The time=30 minute sample of the crude product mixture contains about 43.6% by weight in total of maleate plus malate plus 2,2'-oxodisuccinate plus fumarate, calculated as the anions. The relative weight percentages of the anions are: maleate, 28.3% malate, 27.4% 2,2'-oxodisuccinate, 42.5%; fumarate, 1.8%, i.e., as defined herein, the 2,2'-oxodisuccinate yield at this stage is 42.5%. The total weight of the crude product mixture is about 63800 g. A pH meter reading of about 10.7/78° C. is obtained using a combination electrode (Corning X-EL Cat. No. 476262, calibrated against a pH 10 buffer at 25° C. and a temperature compensated for readings at 78° C.). Note that the meter readings under these conditions of concentration, especially sodium ion concentration, as well as of temperature, are useful numbers for process monitoring, provided that the electrodes used are new or otherwise proven reliable; however, the meter readings are not true pH values.

The second operator ensures that as of the end of the above-mentioned 16 minute cooling period, the crude product mixture is continuously stirred at about 78° C. for 4.5 hours. At this stage, HPLC analysis shows that the 2,2'-oxodisuccinate level has reached about 72% with about 4% fumarate and approximately balanced levels of unreacted maleate and malate also present. The following maturation procedure is now immediately carried out.

(b) Maturation:

Rapidly (less than about 2 hours, more preferably, less than 1 hour), the temperature of the crude product mixture is reduced to approximately 40° C. The crude product mixture is held at this 40° C. temperature for a total maturation time of about 139 hours, measured from the start of cooling in the maturation procedure. During maturation, the crude product mixture is infrequently stirred. (Typically, one-hour periods of stirring precede HPLC sampling on a once-daily basis; the stirring ensures representative sampling.) The 2,2'-oxodisuccinate yield at the end of the 139 hour maturation is about 82%, with less than about 6% fumarate byproduct.

A second maturation stage is undertaken. The crude product mixture is cooled to about 27° C. within 6 hours or less (on small scale versions of this experiment, cooling times can be as short as 10 minutes) and maintained at that temperature, with once-daily stirring prior to HPLC sampling. The second maturation stage has a total duration of about 72 hours. The 2,2'-oxodisuccinate yield is now about 85.3%, with about 6.8% fumarate byproduct. The crude product mixture as sampled at this stage has a density of about 1.50 g/cm$^3$ at 35° C.

A third maturation stage is now undertaken. The crude product mixture is further cooled to about 23° C. and maintained at that temperature, with once-daily sampling as before. The third maturation stage has a total duration of about 95 hours. The 2,2'-oxodisuccinate yield is now about 87%; about 7% fumarate byproduct is present.

Viscosity characterization of crude product mixture:

Brookfield viscosity readings are obtained at t=48 hours/40° C./50 r.p.m.: 1600 cps and t=288 hours/22° C./50 r.p.m.: 7300 cps.

(c) Arresting the Reaction; Inorganic Workup:

To avoid decreasing the 2,2'-oxodisuccinate yield and increasing the fumarate byproduct levels, the reaction is arrested, and simultaneously, calcium levels are depleted, replacing calcium with sodium cations and producing a 2,2'-oxodisuccinate product directly useful as a laundry detergent builder, as follows:

The crude product mixture is diluted with 10000 g distilled water at 25° C., is then siphoned out of the reactor drum, and is further diluted with 76000 g distilled water. Sodium carbonate (14480 g, 136.6 moles, Fisher) and sodium bicarbonate (1036 g, 12.3 moles, Fisher ACS grade) are added at about 70° C. (temperatures such as this help calcium carbonate precipitation in filterable form). A pH meter reading of 9.94/72° C. is obtained. The mixture is stirred for 5 hours at about 70° C. Upon cooling to ambient temperature, the mixture is filtered through two layers of filter paper (E-D Corp., No. 613-20, 60 cm diameter). (The filter cake may be recovered and re-used; see Example 3). The filtrate is evaporated to a volume of about 80 liters. A polishing filtration through coarse frit glass Buchner filters is carried out. The stable, liquid-form finished product 2,2'-oxodisuccinate builder weighs 92117 g (92.1 kg) and analyzes, by weight of organics, 87.1% 2,2'-oxodisuccinate (i.e., yield of the process is 87.1%); 6.7% fumarate, 3.2% maleate and 3.1% malate are also present. The organic composition of the product is not significantly affected by the workup.

EXAMPLE 2

Equipment: Small-scale version of the equipment used in Example 1.

Starting-Materials:

| | |
|---|---|
| Distilled Water: | 108.8 g |
| 50% Aqueous NaOH: | 161.6 g (2.02 moles NaOH) |
| D,L-Malic Acid: | 134.1 g (1.0 mole) |
| Ca(OH)$_2$ | 94.7 g (1.24 moles) |
| Maleic Anhydride: | 117.6 g (1.20 moles) |
| Total Weight: | 616.8 g |
| Weight Percentage of maleate (C$_4$H$_2$O$_4$) plus malate (C$_4$H$_4$O$_5$): | 43.6% |

(a) Contacting and Primary Reaction:

Precontacting:

The 50% aqueous sodium hydroxide is added to the distilled water, with stirring, at about 60° C.–70° C.

The D,L-malic acid, as granules, is stirred in whilst the temperature is maintained in the range about 60° C.–70° C.

The calcium hydroxide is now added, maintaining the temperature and stirring. This precontacting procedure achieves formation of a preformed mixture containing the essential sodium, calcium, malate, alkali (hydroxide) and water components. This mixture is weighed. Now, only the maleate component need be added.

Final Contacting:

Over 20 to 25 minutes, the temperature initially about 60° C., freshly crushed maleic anhydride, in the above-indicated total amount, is added to the preformed mixture of the precontacting procedure. The maleic anhydride is added at a steady rate, with stirring. The reaction mixture is briefly allowed to heat exothermically to a temperature of about 80° C. during the maleic anhydride addition. The weight is checked and a small amount of water is added, to compensate for evaporation loss during the maleic anhydride addition.

(b) Maturation:

During the procedure which follows, the reaction is conducted at approximately constant weight by adding small amounts of water to compensate for evaporation losses as the reaction progresses.

Stirring is maintained and the crude product mixture of step (a) is cooled over a one hour period to a temperature of about 40° C. The reaction vessel and crude product mixture are transferred to an oven, thermostatically controlled at 40° C. The unstirred contents of the reaction vessel are maintained at about 40° C. for a 167-hour period. In an additional maturation step, the reaction vessel and crude product mixture are removed from the oven, are cooled to 25° C. over 1 hour and are then stored without stirring for an additional 168 hours.

(c) Arresting the Reaction; Inorganic Workup:

The procedure (c) of Example 1 is used. The amounts of water, sodium carbonate and sodium bicarbonate are reduced in proportion with the scale and stoichiometry of the process.

HPLC analysis of the product of step (b) reveals that it has a 2,2'-oxodisuccinate yield of about 92% with fumarate byproduct levels of about 4%. About 4% of unreacted maleate and malate are present. The organic analysis is unchanged after workup.

EXAMPLE 3

The equipment described in Example 1 is used.

Precontacting of malate, a little maleate and calcium by preneutralization with calcium carbonate:

To a solution at 70° C. comprising water (18000 g), maleic acid (1622 g, 14 moles) and D,L-malic acid (6700 g, 50 moles) in an open reaction vessel is added slowly over about 30 minutes, with stirring, a filter cake, such as produced in Example 1, containing calcium carbonate (6200 g, 62 moles). Carbon dioxide and a significant fraction of entrained water are allowed to boil off for 30 minutes after completing the addition.

Addition of Sodium Hydroxide:

50% aqueous sodium hydroxide (8760 g, 109.5 moles NaOH) is slowly added to the mixture with stirring. During the sodium hydroxide addition, further loss of water is permitted. The sodium cation-containing alkaline mixture now contains about 12917 g water.

Contacting of the bulk of the maleate and primary 2,2'-oxodisuccinate-forming reaction:

Over a 20 minute period, molten maleic anhydride at about 65° C. (4900 g, 50 moles) is added to the vortex of the stirred mixture at a steady rate. During this period, an exotherm carries the temperature of the reaction from 85° C. to a maximum in the range 103° C.–105° C. and cooling is applied so that at the end of the 20 minute period, reaction temperature is about 76° C.–78° C.

Maturation Procedure:

Rapidly (in less than about 1 hour), the temperature of the crude product mixture is reduced to about 40° C. The crude product mixture is held at about 40° C. for a total duration of the maturation procedure of about 240 hours. The crude product mixture now has a 2,2'-oxodisuccinate yield of about 83%. The product workup is as in Example 1.

EXAMPLES 4, 5, 6 AND 7

Common Procedure: (throughout, evaporation of water is prevented or the water level is adjusted to keep an approximately constant water content of the reaction. Also, HPLC analysis samples are taken at regular intervals. See Example 1 and HPLC Analysis Protocol hereinafter for further details).

Equipment: small-scale version of the equipment used in Example 1.

(a) Contacting and Primary Reaction:

Precontacting:

Add 50% aqueous sodium hydroxide to distilled water with stirring at about 60° C.–70° C.

Stir in D,L-malic acid whilst holding the mixture at a temperature in the range 80° C.–90° C.

Add calcium hydroxide with stirring at about the same temperature.

Stir for 10 minutes.

Final Contacting:

Over 10 to 15 minutes at 85° C., add maleic anhydride at a steady rate with stirring. Allow exothermic heating of the reaction mixture from 85° C. to about 105° C. at least for a brief period during the maleic anhydride addition.

Stir an additional 15 minutes, during which reaction temperature is rapidly brought down to $T_r$.

The above-mentioned 10–15 minutes of maleic anhydride addition plus 15 minutes thereafter constitute $t_c$ (contacting time). The above-mentioned range of contacting temperatures 85° C.–105° C. constitute $T_c$ (contacting temperatures).

Stir at $T_r$ for a period $t_r$: $T_r$ and $t_r$ are as specified below for each example.

(b) Maturation:

Bring temperature to $T_m$ by cooling within 1 hour and maintain this temperature, with or without stirring, for a total duration of the maturation procedure of $t_m$ hours.

(c) Arresting the Reaction; Inorganic Workup:

The procedure (c) of Example 1 is used. The amounts of water, sodium carbonate and sodium bicarbonate are reduced, in proportion with the scale and stoichiometry of the process.

Starting-Materials:

In each of Examples 4, 5, 6 and 7:

| Distilled Water | 115.6 g |
|---|---|
| 50.0% Aqueous NaOH | 156.8 g (1.96 moles NaOH) |
| D,L-Malic Acid | 134.1 g (1.0 mole) |
| Ca(OH)$_2$ | 105.1 g (1.42 moles) |
| Maleic Anhydride | 128.4 g (1.31 moles) |
| Total Weight | 640.0 g |
| Total Weight % of Maleate (as $C_4H_2O_4$) + malate (as $C_4H_4O_5$): | 44.0% |

Temperatures and Times:

In each of Examples 4, 5, 6 and 7: $T_r = 76°$ C.; $t_r = 5$ hours.

Maturation Results:

| Ex. No. | $T_m$ (°C.) | $t_m$ (hours) | % ODS* | Composition by HPLC, % | | |
|---|---|---|---|---|---|---|
| | | | | maleate | malate | fumarate |
| 4 | 25 | 168 | 84.4 | 7.8 | 4.2 | 3.7 |
| 5 | 40 | 120 | 86.0 | 5.3 | 3.7 | 5.0 |
| 6 | 50 | 72 | 83.0 | 4.3 | 5.6 | 7.2 |
| 7 | 60 | 24 | 81.6 | 5.3 | 6.5 | 6.7 |

*2,2'-oxodisuccinate

In the above, at the indicated maturation times, the 2,2'-oxodisuccinate yields are still increasing in the 25° C. and 40° C. examples, whereas in the 50° C. and 60° C. examples, the 2,2'-oxodisuccinate yields are near or at their maxima.

EXAMPLE 8

The procedures (a), (b) and (c) of Examples 4, 5, 6 and 7 are carried out with the following modifications:

Contacting time $t_c$ is about 30 minutes.

Contacting temperatures $T_c$ are in the range from about 75° C. to about 110° C., provided that the reaction mixture is cooled sufficiently so that the temperatures do not exceed about 100° C. for more than 15 minutes and do not exceed 80° C. for more than 30 minutes.

The optional stirring period $t_r$ is not used in this Example ($t_r = 0$ minutes).

$T_m$ is about 40° C.

Amounts of Starting-Materials:

| Distilled Water | 121.9 g |
|---|---|
| 50% Aqueous NaOH | 156.8 g (1.96 moles NaOH) |
| D,L-Malic Acid | 134.1 g (1.0 mole) |
| Ca(OH)$_2$ | 105.1 g (1.42 moles) |
| Maleic Anhydride | 128.4 g (1.31 moles) |
| Total Weight | 646.3 g |

Results:

| Tm °C. | Tm hr | % ODS* | % maleate | % malate | % fumarate |
|---|---|---|---|---|---|
| 40° | 48 | 83.3 | 10.8 | 3.5 | 2.3 |
| 40° | 120 | 85.7 | 5.8 | 3.9 | 4.6 |

*2,2'-oxodisuccinate

EXAMPLE 9

Preparation of a Calcium malate-hydroxide-Containing Starting-Material

Maleic anhydride (29.4 g, 0.3 moles, Aldrich) is dissolved in distilled water by heating to about 85° C.–90° C. in an open preweighed Hastalloy C autoclave (Parr instrument Co., Model 4561, 300 cc) and stirring. The solution is cooled by placing the autoclave in an icebath. When a temperature of 60° C.–80° C. is reached, calcium hydroxide (33.3 g, 0.45 moles, Aldrich, A.C.S.) addition is started. A thick paste forms, which thins significantly as addition of calcium hydroxide progresses. When all the calcium hydroxide is added, the total reaction weight is corrected by adding water to a reaction weight of 192.0 g. The water content is calculated as 70.2%. The autoclave is sealed, placed in a 165° C. thermostat-equipped oil bath and stirred. After bringing the reaction mixture to equilibrium with the oil bath temperature, further stirring is continued for 4.5 hours (the reaction time as defined herein). Note that the oil bath and autoclave are previously calibrated: it is shown that an oil bath temperature of about 165° C. corresponds with an internal autoclave temperature of about 145° C. Pressure reaches a maximum of 45 psig (0.31 MPa; where 1 psi=0.006895 MPa). The autoclave is cooled in water, opened, and weighed. The weight is within 2 g; insignificant leakage of the autoclave is thereby demonstrated. The contents of the autoclave are comprised primarily of a granular product, white in color and odorless. No off-odors are detected. (When very high temperatures, 185° C. or more, are used, the product acquires trace odor and trace impurity peaks in HPLC analysis). The autoclave also contains some finer solids and a thin crust on the internal walls. All contents are readily scraped out, are filtered to remove mother liquors of the reaction, and are air dryed. Analysis indicates that by weight % of organic components, the product comprises 94.7% malate. 2.1% 2,2'-oxodisuccinate and 3.2% fumarate are copresent. No maleate is detected. The inorganic composition is approximately as determined on the basis of the amounts of calcium and hydroxide excess used.

X-ray Diffraction Characterization of the Starting-Material

Air-dried samples of the solid product of Example XV are gently ground, using an agate pestle and mortar, and packed in a sample planchette. X-ray diffration data are collected using a computer-controlled STOE diffractometer with diffracted-beam graphite monochromator; $CuK_\alpha$ radiation; X-ray generator at 40 kV/37 mA; scan range 1°–70° in $2\theta$ at a rate of 0.04/step and counting time 4 seconds/step.

The X-ray diffraction pattern has a major spacing of 8.597 Å ($2\theta=10.28°$) inconsistent with any known crystal form of calcium malate, calcium malate hydrate, malic or maleic acids, calcium hydroxide or calcium oxides in the JCPDS International Centre for Diffraction Data, 1601 Park Lane, Swarthmore, PA, 19081 (formerly Joint Committee on Powder Diffraction Standards) reference files.

Process According to the Invention

Dry granular "calcium malate" prepared as described above is finely ground using a pestle and mortar and converted to 2,2'-oxodisuccinate as follows. The ground material (66.24 g; equivalent to 0.3 moles content of calcium malate and 0.15 moles content of Ca(OH)$_2$, 34 cm$^3$ H$_2$O and 38.8 g (0.48 moles), NaOH as 50% aqueous solution (Fisher), are mixed together in a glass or stainless steel reaction vessel equipped with a stirrer, reflux condenser and heating oil bath. Powdered calcium hydroxide (2.44 g, 0.33 moles, Aldrich) is mixed in. The reaction vessel is heated, with stirring, to a temperature of about 70° C.–80° C.; at which point a milky or chalky suspension is observed. Crushed, powdered maleic anhydride (36.5 g, 0.37 moles, Aldrich) is added over 5–10 minutes in small portions. Though the reaction is exothermic and may briefly reach temperatures close to reflux temperature, good stirring and thermostatting of the heating bath ensures that the mixture equilibrates rapidly at the 70° C.–80° C. range. During the last 3 minutes of maleic anhydride addition, a light amber homogeneous crude product mixture, substantially clear to the eye, is formed.

As soon after completion of the maleic anhydride addition as the homogeneous crude product mixture is formed, the mixture is cooled to about 30° C. The mixture is maintained at the new, lower temperature for a period of about 21 days. HPLC analysis now gives the following results: 88.0% 2,2'-oxodisuccinate; 3.0% maleate; 3.0% malate and 6.0% fumarate.

The crude product mixture is now treated with excess aqueous NaHCO$_3$/Na$_2$CO$_3$ giving a mixture having a pH of about 10. This is heated for about 4 hours at 70° C. with stirring, producing tetrasodium 2,2'-oxodisuccinate and inorganic precipitate which is separated by filtration. The solution of product is conventionally dried.

EXAMPLE 10

Equipment: Small-scale version of the equipment used in Example 1.

Precontacting of maleate and sodium by preneutralization of maleic acid with sodium carbonate to form disodium maleate in-situ:

To a solution at 80° C., made from distilled water (300 grams) and maleic acid (148.5 grams, 1.28 moles) in a weighed, open reaction vessel is added slowly, over about 30 minutes, with vigorous stirring, sodium carbonate (116.6 grams, 1.10 moles). Carbon dioxide and a significant fraction of entrained water are allowed to boil off for 30 minutes after completing the addition.

Addition of calcium hydroxide:

Calcium hydroxide (91.8 grams, 1.24 moles) is slowly added to the mixture with stirring. During the next hour, water is evaporated at 70° C. to 80° C. under a stream of compressed air, so that the total weight of the contents of the reaction vessel is reduced to about 504 grams.

Addition of malate and primary 2,2'-oxodisuccinate-forming reaction:

Over a 10 minute period, D,L-malic acid (134.1 grams, 1.0 mole) is added at a steady rate to the vortex of the stirred reaction mixture, held at about 100° C. After adding the D,L-malic acid, the temperature of the crude product mixture is reduced over a 10 minute period to about 78° C. Stirring is continued at about 78° C. for a 5 hour period.

Maturation procedure:

Rapidly (in less than 1 hour), the temperature of the crude product mixture is reduced to about 50° C. The crude product mixture is held at about 50° C. for a total duration of the maturation procedure of about 72 hours.

The crude product mixture now has a 2,2'-oxodisuccinate yield of about 82%, as determined by HPLC. The product workup is a scaled-down version of procedure (c) in Example 1.

EXAMPLE 11

Equipment: Scaled-down version of the equipment used in Example 1.

Over a 25 minute period at approximately constant temperature of 49° C., maleic anhydride powder (125.4 grams, 1.28 moles) is added steadily, with stirring, to a mixture preformed by combining:

| | |
|---|---|
| distilled water | 111.5 grams |
| 50% aqueous NaOH | 175.2 grams (2.19 moles) |
| D,L-malic acid | 134.1 grams (1.0 mole) |
| calcium hydroxide | 91.8 grams (1.24 moles) |

The temperature and stirring are maintained for 120 hours, whereupon the crude product mixture which is formed has a HPLC-based 2,2'-oxodisuccinate yield of about 82%.

The reaction is arrested without delay, and the crude product mixture is converted to tetrasodium 2,2'-oxodisuccinate by successively (i) treating with sodium carbonate/bicarbonate; (ii) filtering to remove the precipitated calcium carbonate and (iii) conventionally drying the flitrate.

EXAMPLE 12

D,L-malic acid, 134.1 grams, 1.0 mole, is dissolved in 111.5 grams of water in a suitably sized stainless steel reaction vessel equipped with stirring and temperature control means (see Example 1). As rapidly as possible, a slurry made by separately mixing sodium hydroxide (175.2 grams, 50% aqueous solution, 2.19 moles NaOH content) and calcium hydroxide (91.8 grams, 1.24 moles) is added whilst stirring is continued and the temperature is held at about 75° C. With the mixture and maleic anhydride both at temperatures in the range 60° C.–70° C., molten maleic anhydride, 125.4 grams, 1.28 moles, is added at a steady rate with continuous stirring over a period of about 20 minutes. The temperature and stirring are maintained for a further 10 minutes. The temperature is now permitted to fall to about 50° C. over a 2 hour period, and the crude product mixture, now almost clear and somewhat more viscous than heretofore, is stirred at about 50° C. for 94 hours. The temperature is now further quickly reduced to about 40° C., and the crude product mixture is stored, unstirred, for about 144 hours. The reaction is arrested and the crude product mixture is worked up by sodium carbonate/bicarbonate treatment as in Example 11. At the time of arresting the reaction, the crude product mixture has a HPLC-analyzed organic composition as follows: 2,2'-oxodisuccinate: 88.7%; maleate: 6.7%; malate: 1.8%; fumarate: 2.7%. After workup, the organic analysis is essentially unchanged.

HPLC Analytical Procedures

High Performance Liquid Chromatography (HPLC) analyses herein for maleate, malate, 2,2'-oxodisuccinate and fumarate are readily reproduced using the following conditions, by an analyst familiar with HPLC instrumentation:

Column: Two Supelco LC18 4.6 mm I.D.×25 cm columns equilibrated with mobile phase for about 10 days at a flow rate of about 0.2 ml/min Mobile Phase: 0.01–0.04N $H_2SO_4$ in distilled/deionized water. The sulfuric acid concentration is adjusted in dependence of the age of the columns to give separation of each of the organic species analyzed.

Flow Rate: 1 ml/min

Pump: A single Waters 6000A or 510

Injector: Waters Wisp 710, injection volume 25 ul

Detector: Refractive-Index Detector; Spectra-Physics 6040XR.

Integrator: Waters 730 Data Module

Sample Preparation: For distribution analysis: ca 0.5 g of crude product mixture is removed from the reaction vessel and is quenched by adding to 100 ml 0.1N sulfuric acid; for concentration analysis: weigh a known amount into a 10 ml volumetric flask to give a peak area that falls within the calibration curve, q.s. with 0.1N sulfuric acid. In both cases, the final solution pH is about 2.

Calculations:

Distribution analysis: Divide peak area for a single species; i.e., maleate, fumarate, 2,2'-oxodisuccinate, malate, by total area for all peaks. This assumes equivalent refractive index response factors for all species; the assumption is proved to be an excellent approximation by concentration analysis. Based on this assumption, the distribution analysis corresponds to the relative weight percentage of the maleate, malate, 2,2'-oxodisuccinate and fumarate analyzed.

Concentration analysis: A direct calibration curve is made for maleic acid, malic acid, and fumaric acid for direct correlation of peak areas to concentration expressed as percentage by weight.

The same procedure is used to determine the weight % of 2,2'-oxodisuccinate except that 1,2,3,4-butanetetracarboxylic acid (structurally similar to 2,2'-oxodisuccinate) or chromatographically pure 2,2'-oxodisuccinate is used as the calibration species. Note that use of 1,2,3,4-butanetetracarboxylic acid as a reference material assumes that 2,2'-oxodisuccinate and 1,2,3,4-butanetetracarboxylic acid have similar refractive index response factors. In all cases, a linear regression analysis is used to fit the curves.

Correspondence between the results obtained for the distribution analysis and the concentration analysis is very good for a given sample. In view of the good correspondence, the tables and text herein report only the simple distribution analysis results.

What is claimed is:

1. In an aqueous process for manufacturing 2,2'-oxodisuccinate by reacting starting-materials comprising the components:
   I. an organic starting-material component comprising maleate;
   II. a divalent metal cation component; and
   III. an alkali component, to achieve the partial conversion of the organic starting-material component to 2,2'-oxodisuccinate, said process tending to form a fumarate byproduct, the improvement whereby a 2,2'-oxodisuccinate yield of about 80% or higher is secured, said improvement comprising:
   A. selecting starting-materials which comprise:
      I. an organic comprising maleate and preformed malate at a maleate:malate mole ratio in the range from about 0.7:1 to about 2.0:1;

II. a divalent metal cation component selected from calcium, magnesium and mixtures thereof at a divalent cation component:organic component mole ratio in the range from about 0.1:1 to about 0.95:1;

III. an alkali component selected from hydroxide and hydroxide-forming anions; and, additionally, IV. a solubilizing monovalent cation component selected from sodium, potassium and mixtures thereof; and B. conducting the process in a fluid, aqueous alkaline mixture of said starting-materials having the following net concentrations by weight:

water:
no more than about 75%;

alkali component III, expressed as net excess hydroxide:
at least about 0.0001%; and solubilizing monovalent cation component IV:
at least about 1%; and reacting said mixture B for a period sufficient to attain said 2,2'-oxodisuccinate yield at temperatures in the range from about 20° C. to about 110° C., and arresting the reaction;

provided that the total duration of reaction is not less than about 12 hours an not more than about 400 days and further provided that:

the total time at any temperature above about 100° C. does not exceed about 1.5 hours and the total time at any temperature above about 90° C. does not exceed about 4.5 hours and the total time at any temperature above about 80° C. does not exceed about 13.5 hours and the total time at any temperature above about 70° C. does not exceed about 1.7 days and the total time at any temperature above about 60° C. does not exceed about 5.1 days and the total time at any temperature above about 50° C. does not exceed about 15 days and the total time at any temperature above about 40° C. does not exceed about 46 days and the total time at any temperature above about 30° C. does not exceed about 137 days.

2. A process according to claim 1

A. selecting starting-materials which comprise:

I. an organic component comprising maleate and preformed malate at a maleate:malate mole ratio in the range from about 0.9:1 to about 1.8:1;

II. a divalent metal cation component selected from calcium and mixtures thereof with magnesium, the calcium:magnesium mole ratio ranging from about 1.0:0.0 to about 0.9:1; at a divalent cation component:organic component mole ratio in the range from about 0.2:1 to about 0.85:1;

III. an alkali component selected from hydroxide and hydroxide-forming anions; and, additionally, IV. a solubilizing monovalent cation component selected from sodium and mixtures thereof with potassium, the sodium:potassium mole ratio ranging from about 1.0:0.0 to about 0.9:0.1; and B. conducting the process in a fluid, aqueous alkaline mixture of said starting-materials having the following net concentrations by weight:

water:
from about 25% to about 60%;

alkali component III, expressed as net excess hydroxide;
from about 0.0001% to about 2%; and solubilizing monovalent cation component IV:
from about 3% to about 20%; and reacting said mixture at temperatures in the range about 20° C. to about 110° C. for a period sufficient to attain said 2,2'-oxodisuccinate yield, and arresting the reaction;

provided that the total duration of reaction is not less than about 12 hours and not more than about 240 days and further provided that:

the total time at any temperature above about 100° C. does not exceed about 1 hour and the total time at any temperature above about 90° C. does not exceed about 3 hours and the total time at any temperature above about 80° C. does not exceed about 8 hours and the total time at any temperature above about 70° C. does not exceed about 1 day and the total time at any temperature above about 60° C. does not exceed about 3 days and the total time at any temperature above about 50° C. does not exceed about 9 days and the total time at any temperature above about 40° C. does not exceed about 27 days and the total time at any temperature above about 30° C. does not exceed about 81 days.

3. A process according to claim 2

A. selecting starting-materials which comprise:

I. an organic component comprising maleate and preformed malate at a maleate:malate mole ratio in the range from about 1.05:1 to about 1.7:1;

II. a divalent metal cation component selected from calcium at a divalent cation component:organic component mole ratio in the range from about 0.25:1 to about 0.80:1;

III. an alkali component selected from hydroxide and hydroxide-forming anions; and, additionally, IV. a solubilizing monovalent cation component selected from sodium; and B. conducting the process in a fluid, aqueous alkaline mixture of said starting-materials having the following net concentrations by weight:

water:
from about 30% to about 50%;

alkali component III, expressed as net excess hydroxide:
from about 0.01% to about 1.5%; and solubilizing monovalent cation component IV:
from about 3% to about 16%; and reacting said mixture at temperatures in the range about 20° C. to about 110° C. for a period sufficient to attain said 2,2'-oxodisuccinate yield, and arresting the reaction;

provided that the total duration of reaction is not less than about 12 hours and not more than about 40 days and further provided that:

the total time at any temperature above about 100° C. does not exceed about 30 minutes and the total time at any temperature above about 90° C. does not exceed about 1.5 hours and the total time at any temperature above about 80° C. does not exceed about 5 hours and the total time at any temperature above about 70° C. does not exceed about 15 hours and the total time at any temperature above about 65° C. does not exceed about 1 day and the total time at any temperature above about 60° C. does not exceed about 1.5 days and the total time at any temperature above about 50° C. does not exceed about 8 days.

4. A process according to claim 3
A. selecting starting-materials which comprise:
  I. an organic component comprising maleate and preformed malate at a maleate:malate mole ratio in the range from about 1.1:1 to about 1.6:1;
  II. a divalent metal cation component selected from calcium, at a divalent cation component:organic component mole ratio in the range from about 0.35:1 to about 0.80:1;
  III. an alkali component selected from hydroxide and hydroxide-forming anions; and, additionally,
  IV. a solubilizing monovalent cation component selected from sodium; and
B. conducting the process in a fluid, aqueous alkaline mixture of said starting-materials having the following net concentrations by weight:
  water:
    from about 30% to about 45%;
  alkali component III, expressed as net excess hydroxide:
    from about 0.05% to about 1%; and
  solubilizing monovalent cation component IV:
    from about 3.5% to about 12%.

5. A process according to claim 4 wherein said components are reacted non-isothermally; said process further being characterized in that it comprises the steps of
  (a) in an elevated temperature primary reaction procedure of duration about 10 minutes to about 8 hours, at about 50° C. to about 110° C., contacting said starting-materials to form said fluid, aqueous alkaline mixture and reacting to form a crude product mixture which remains fluid, comprising freshly formed 2,2':oxodisuccinate together with unreacted maleate and malate and immediately
  (b) in a lower temperature maturation procedure of duration about 1 day to about 30 days, reduction the temperature of said crude product mixture of step (a) in one or more steps whilst retaining fluidity and continuing to react said crude product mixture, for a period sufficient to chemically combine and form 2,2'-oxodisuccinate from said maleate and malate; thereby increasing the overall proportion of 2,2'-oxodisuccinate present in said crude product mixture while achieving control of the rate of formation of fumarate byproduct; and
  (c) arresting said lower temperature maturation procedure.

6. A process according to claim 5 wherein said lower temperature maturation procedure (b) comprises reducing the temperature of said crude product mixture of step (a) to temperatures in the range from about 20° C. to about 45° C. and wherein said starting-materials comprise:
  I. an organic component comprising maleate and preformed malate at a maleate:malate mole ratio in the range from about 1.15:1 to about 1.40:1;
  II. a divalent metal cation component selected from calcium, at a divalent cation component:organic component mole ratio in the range from about 0.41:1 to about 0.76:1;
  III. an alkali component selected fromm hydroxide and hydroxide-forming anions; and, additionally,
  IV. a solubilizing monovalent cation component selected from sodium;

and wherein said process is conducted in a fluid, aqueous alkaline mixture of said starting-materials having the following net concentrations by weight:
  water:
    from about 35.0% to about 41.0%;
  alkali component III, expressed as net excess hydroxide:
    from about 0.10% to about 0.91%; and
  solubilizing monovalent cation component IV:
    from about 3.9% to about 10.6%.

7. A process according to claim 6 wherein step (a) is carried out at elevated temperatures in the range of from about 50° C. to about 110° C. and has a duration of from about 10 minutes to about 5 hours, provided that in step (a), said elevated temperatures are not in excess of about 100° C. for times greater than about 15 minutes and are not in excess of about 80° C. for times greater than about 30 minutes; and
wherein step (b) comprises reducing the temperature to lower temperatures in the range of from about 20° C. to about 40° C. in a time less than about 2 hours and maintaining said lower temperatures; step (b) having a duration of from about 1 day to 21 days in total; provided that in step (b), said lower temperatures are not in excess of about 36° C. for times greater than about 7 days and are not in excess of about 30° C. for times greater than about 14 days.

8. A process according to claim 7 wherein said starting-materials comprise at least one maleate compound selected from the group consisting of maleic anhydride and maleic acid, together with at least one malate compound selected from the group consisting of malic acid and stereoisomers thereof.

9. A process according to claim 8 wherein said starting-materials comprise at least one sodium-containing compound selected from the group consisting of disodium maleate, disodium malate, sodium carbonate, sodium bicarbonate and sodium hydroxide.

10. A process according to claim 9 wherein said starting-materials consist essentially of maleic anhydride, D,L-malic acid, sodium hydroxide and calcium hydroxide and wherein in step (a), said elevated temperature reaction procedure comprises adding maleic anhydride over a period of about 10 to about 30 minutes, as portions of solid or as liquid at temperatures above the melting-point but not exceeding about 100° C., to a continuously stirred preformed mixture of said D,L-malic acid, calcium hydroxide and sodium hydroxide, the preformed mixture having an initial temperature in the range from about 50° C. to about 85° C., rising exothermically to a maximum of from about 100;20 C. to about 110° C. during the course of maleic anhydride addition, thereby forming a crude product mixture.

11. A process according to claim 10 wherein upon ending step (a), said crude product mixture is substantially homogeneous and has an organic composition, as a percentage by weight based on 2,2'-oxodisuccinate plus maleate plus malate plus fumarate, of:
  2,2'-oxodisuccinate: from about 20% to about 45%;
  fumarate: from about 1% to about 2% and
  maleate plus malate: from about 53% to about 79%.

12. A process according to claim 10 wherein step (b) comprises cooling said crude product mixture to a lower temperature of from about 36° C. to about 40° C. within a time of about 10 minutes to about 2 hours, and storing said crude product mixture at said lower temperature; step (b) having a duration of from about 2 days to about 7 days in total.

13. A process according to claim 12 wherein said crude product mixture at the end of step (b) has an organic composition comprising, as a percentage by weight based on 2,2'-oxodisuccinate plus maleate plus malate plus fumarate, of:
  2,2'-oxodisuccinate: at least about 82%;
  fumarate: from about 1.5% to about 5.7% and
  maleate plus malate: from about 7.3% to about 16.5%.

14. A process according to claim 10 wherein step (b) comprises:
  (i) cooling said crude product mixture to a first lower temperature in the range from about 36° C. to about 40° C. within a time of about 10 minutes to about 1 hour, and storing said crude product mixture at said first lower temperature; step (i) having a duration of from about 2 days to about 7 days;
  (ii) followed immediately by cooling said crude product mixture to a second lower temperature in the range from about 25° C. to about 30° C. within a time of about 10 minutes to about 6 hours, and storing said crude product mixture at said second lower temperature; step (ii) having a duration of from about 7 days to about 14 days.

15. A process according to claim 14 wherein said crude product mixture at the end of step (b) has an organic composition comprising, as a percentage by weight based on 2,2'-oxodisuccinate plus maleate plus malate plus fumarate, of:
  2,2'-oxodisuccinate: at least about 90%;
  fumarate: from 2% to about 6% and
  maleate, malate or mixtures thereof: to 100%.

16. A process according to claim 14 comprising arresting step (b) by treating said crude product mixture with a warm aqueous mixture of sodium carbonate and sodium bicarbonate, thereby precipitating calcium carbonate.

17. A process according to claim 6 wherein the starting-materials comprise no more than about 0.01 moles of fumarate impurity per mole of said maleate plus said preformed malate, and wherein step (a) is carried out at elevated temperatures in the range from about 50° C. to about 110° C., provided that in step (a), said elevated temperatures are not in excess of about 100° C. for times greater than about 15 minutes and are not in excess of about 80° C. for times greater than about 1 hour; and
  wherein step (b) comprises reducing the temperature to lower temperatures in the range of from about 20° C. to about 40° C., provided that in step (b), said lower temperatures are not in excess of about 36° C. for times greater than about 7 days and are not in excess of about 30° C. for times greater than about 14 days; step (a) being ended and step (b) being undertaken at any time corresponding with a net increase in fumarate level, based upon HPLC-analysis of the crude product mixture, in the range from about 0.5% to 5%.

18. A process according to claim 17 wherein step (a) is ended and step (b) is undertaken at any time corresponding with a net increase in fumarate level, based upon HPLC-analysis of the crude product mixture, in the range from about 0.5% to 2.5%; and wherein step (b) is ended and step (c) is undertaken immediately upon reaching an HPLC-based 2,2'-oxodisuccinate yield of at least about 85%.

19. An isothermal process according to claim 4 wherein the divalent cation component:organic component mole ratio is in the range from about 0.40:1 to about 0.75:1, conducting said process at a concentration of water in the range from about 35% to about 41% and reacting said mixture at a temperature in the range from about 50° C. to about 68° C. for a period of from about 48 hours to about 240 hours.

20. A process according to claim 5 wherein step (a) is carried out at elevated temperatures in the range from about 70° C. to about 110° C., in a period of from about 4 hours to about 5 hours, provided that in step (a), said elevated temperatures are not in excess of about 100° C. for times greater than about 15 minutes and are not in excess of about 80° C. for times greater than about 30 minutes; and
  wherein step (b) comprises reducing the temperature to lower temperatures in the range of from about 50° C. to about 59° C. in a period of from about 15 minutes to about 1 hour, and maintaining said lower temperatures; step (b) having a duration of from about 7 hours to about 20 hours in total.

21. A process according to claim 6 wherein step (a) is carried out at elevated temperatures in the range from about 75° C. to about 110° C., in a period of from about 20 minutes to about 1 hour, provided that in step (a), said elevated temperatures are not in excess of about 100° C. for times greater than about 15 minutes and are not in excess of about 80° C. for times greater than about 30 minutes; and
  wherein step (b) comprises reducing the temperature to lower temperatures in the range of from about 35° C. to about 45° C. in a period of from about 15 minutes to about 1 hour, and maintaining said lower temperatures; step (b) having a duration of from about 48 hours to about 240 hours in total; whereby a 2,2'-oxodisuccinate yield of at least about 85% is secured.

22. An improved aqueous process for preparing 2,2'-oxodisuccinate comprising reacting preformed malic acid, sodium hydroxide, a maleate reactant selected from maleic anhydride, maleic acid and mixtures thereof, and a calcium reactant selected from calcium carbonate and mixtures thereof with calcium hydroxide, according to the immediately consecutive steps:
  (i) mixing calcium carbonate, water, malic acid and a proportion of said maleate reactant, allowing complete evolution of carbon dioxide and forming an acidic mixture;
  (ii) adding sodium hydroxide or a mixture thereof with calcium hydroxide, to the acidic mixture of step (i), forming a sodium cation-containing alkaline mixture;
  (iii) in a period of duration about 1 hour or less, adding the remainder of said maleate reactant to the stirred sodium cation-containing alkaline mixture of step (ii), at temperatures in the range from about 75° C. to about 110° C., having at the end of the step (iii) addition a net hydroxide excess $M_{OH}$;
  (iv) in a period of duration about 1 hour or less, cooling the mixture formed in step (iii) to a temperature in the range from about 35° C. to about 45° C.;
  (v) at said temperature in the range from about 35° C. to about 45° C., continuing to react the mixture of step (iv); the duration of step (v) being from about 48 hours to about 240 hours, whereby a crude product having a HPLC yield of at least 80% 2,2'-oxodisuccinate is secured;

(vi) diluting the product of step (v) with water and precipitating calcium carbonate therefrom; thereby arresting the step (iv) reaction and depleting the level of calcium;

provided that in steps (iii) and (iv) together;

the total time at any temperature above about 100° C. does not exceed about 15 minutes;

the total time at any temperature above about 90° C. does not exceed about 30 minutes;

the total time at any temperature above about 80° C. does not exceed about 2 hours;

the total time at any temperature above about 70° C. does not exceed about 6 hours;

the total time at any temperature above about 65° C. does not exceed about 12 hours; and provided that for each mole of preformed malic acid reacted, the total molar amount of maleate reactant, is about 1.1 to about 1.6 moles;

the total molar amount of calcium reactant, is from about 0.9 to about 1.65 moles;

the total molar amount of sodium hydroxide, is from about 0.92 to about 3.7 moles;

the net hydroxide excess in step (iii), $M_{OH}$, is from about 0.02 to about 0.3 moles; and further provided that for each mole of preformed malic acid reacted, the total net amount of water added in steps (i), (ii) and (iii) together, allowing for evaporation losses, is no less than about 189 grams and no more than about 282 grams.

23. A process according to claim 22 comprising the steps (vii) filtering the mixture of step (vi) to secure a filter-cake and (viii) using the filter-cake of step (vii) as recycled source of calcium carbonate in step (i).

24. The process of claim 5 wherein the mixture formed upon mixing said components in step (a) is a two-phase mixture consisting of a liquid phase, in major proportion, and a solid phase, in minor proportion; the proportion of said solid phase decreasing and the viscosity of said liquid phase increasing so that at the end of step (a), a crude product mixture is formed which is pumpable and which appears substantially homogeneous to the eye.

25. The process of claim 24 wherein the Brookfield relative viscosity of said crude product mixture increases during said lower temperature maturation procedure (b), from an initial value of less than about 100 centipoise to a final value in the range about 1000 centipoise to about 100,000 centipoise, said Brookfield relative viscosity being measured at 22° C./20 r.p.m.

26. A process according to claim 4 wherein said process is conducted in a fluid, aqueous alkaline mixture of said starting-materials, having a composition comprising, by weight, expressed on a fully hydrolyzed and neutralized basis assuming no 2,2'-oxodisuccinate, fumarate or malate formation:

water: from about 30.0% to about 45.0%;

net excess hydroxide: from about 0.05% to about 1.0%;

sodium: from about 3.4% to about 13%;

calcium: from about 4.5% to about 13%;

maleate: from about 19.1% to about 28.4% and preformed malate: from about 16.5% to about 26.8%.

27. A process according to claim 26, wherein said fluid aqueous alkaline mixture optionally comprises:

recycled 2,2'-oxodisuccinate: from about 0% to about 2% and recycled fumarate: from about 0% to about 2%.

* * * * *